US007776556B2

(12) United States Patent
Heikkinen et al.

(10) Patent No.: US 7,776,556 B2
(45) Date of Patent: Aug. 17, 2010

(54) METHOD FOR DIAGNOSING DISEASES

(75) Inventors: Anne Heikkinen, Oulu (FI); Hongmin Tu, Oulu (FI); Taina Pihlajaniemi, Oulunsalo (FI)

(73) Assignee: University of Oulu, Oulu (FI)

( * ) Notice: Subject to any disclaimer, the term of this patent is extended or adjusted under 35 U.S.C. 154(b) by 0 days.

(21) Appl. No.: 12/075,970

(22) Filed: Mar. 14, 2008

(65) Prior Publication Data

US 2008/0227105 A1    Sep. 18, 2008

Related U.S. Application Data

(60) Provisional application No. 60/918,103, filed on Mar. 15, 2007.

(51) Int. Cl.
 *G01N 33/53* (2006.01)
(52) U.S. Cl. .................. 435/7.1; 435/7.2; 435/7.91
(58) Field of Classification Search ............... None
 See application file for complete search history.

(56) References Cited

U.S. PATENT DOCUMENTS 4,208,479 A * 6/1980 Zuk et al. ............... 435/7.9

OTHER PUBLICATIONS

De Bellis, A. et al. Serum antibodies to collagen XIII . . . Clinical Endocrinology (2005) 62,24-29.
Hagg P. et al. Type XIII Collagen is identified as plasma membrane . . . The Journal of Biological Chemistry (1998) 273,25: 15590-15597.
Hagg, P. et al. Type XIII collagen: a novel cell adhesion component . . . Matrix Biology (2001) 19: 727-742.
Jaretzki III, A.,et al. Myasthenia gravis. Recommendations for clinical . . . Neurology (2000) 55: 16-23.
Juvonen, M. et al. Location and Alternative Splicing of Type XIII Collagen . . . Laboratory Investigations (1993) 69(5): 541-551.
Kvist, A-P. et al. Complete exon-intron organization and chromosomal . . . Matrix Biology (1999) 118: 261-274.
Kvist, A.-P. et al. Lack of cytosolic and transmembrane domains . . . American Journal of Pathology (20010 150(4): 1581-1592, Year 2001.
Latvanlehto, A. Type XIII Collagen. 2004. Dissertation. Faculty of Medicine, Dept. of Medical Bioshemisty and Molecular Biology, University of Oulu, Finland.
Nagy A. et al. Derivation of completely cell culture-derived mice . . . Proc Natl Acad Sci (1993). 90: 8424-8428.
Peltonen, S. et al. A novel component of epidermal cell-matrix and cell-cell contact. The Journal of Investigative Dermatology (1999) 113(4): 635-642.
Potocnik A. et al. Fetal and Adult Hematopoietic Stem Cells . . . Immunity (2000) 12: 653-663.
Sakai K. and Miyazaki J-i. A transgenic mouse line that retains Cre recombinase activity . . . Biochemical and Biophyscial Res. Communcations (1997) 237: 318-324.
Gossler, A. and Zachgo, J. Gene and enhancer trap screens in ES cell chimeras. In Joyner A. L. (Ed) 1983. Gene Targeting. A practical approach.

* cited by examiner

*Primary Examiner*—Jacob Cheu
(74) *Attorney, Agent, or Firm*—Dodds & Associates; Leea S. Somersalo; John Dodds

(57) ABSTRACT

An improved method for diagnosing autoimmune or genetic diseases is provided in this disclosure. In particular, a method to diagnose diseases affecting the tissues of organs selected from the group of spleen, brain, heart, kidney, thyroid, eye, skin, intestine, liver, pancreas, adrenal gland, prostate and lungs or from the tissues selected from the group of muscles and bones or other tissues. More specifically, the present invention provides an improved method for diagnosing diseases affecting neuromuscular junctions.

6 Claims, 11 Drawing Sheets

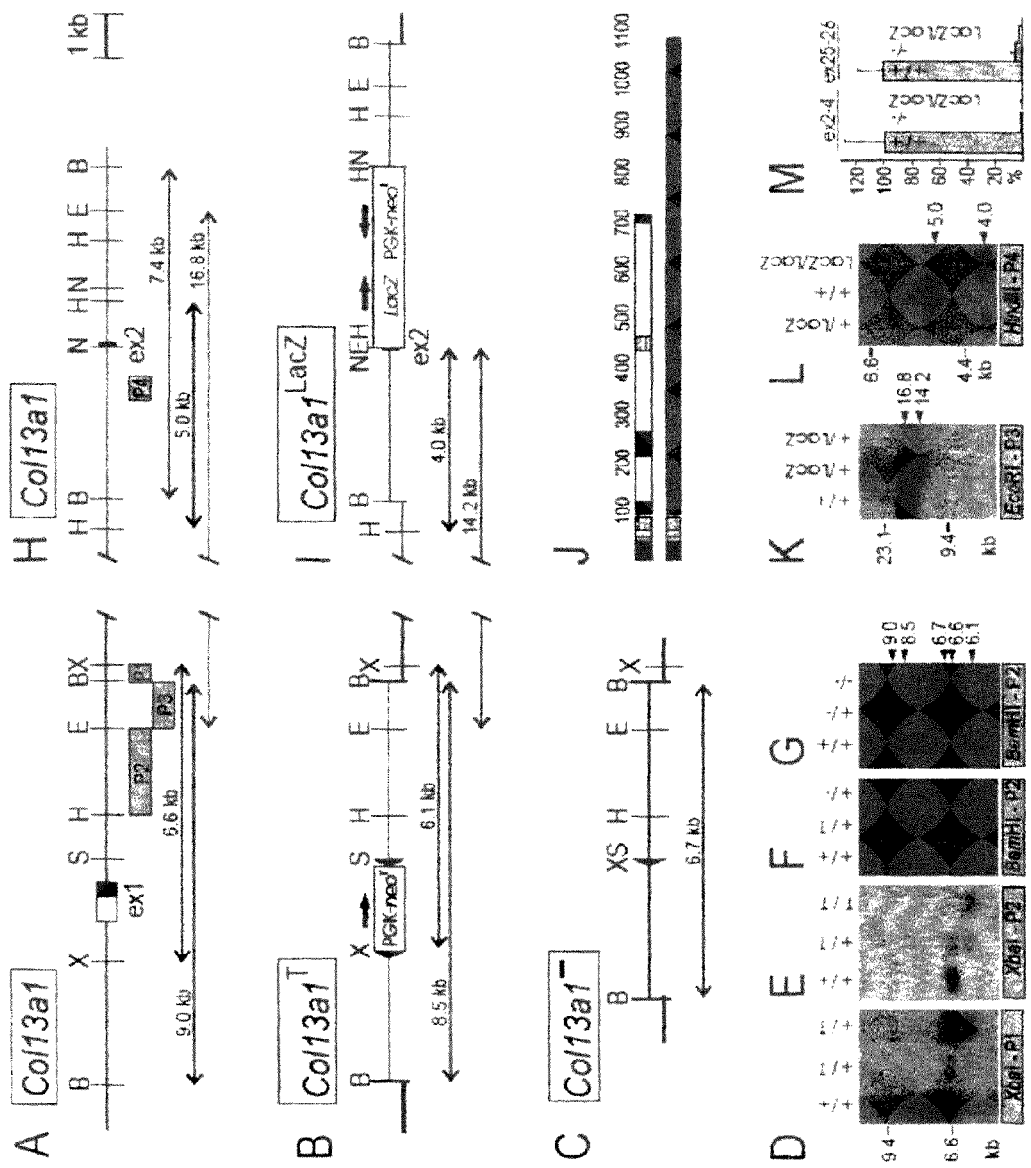
Fig. 1A-M

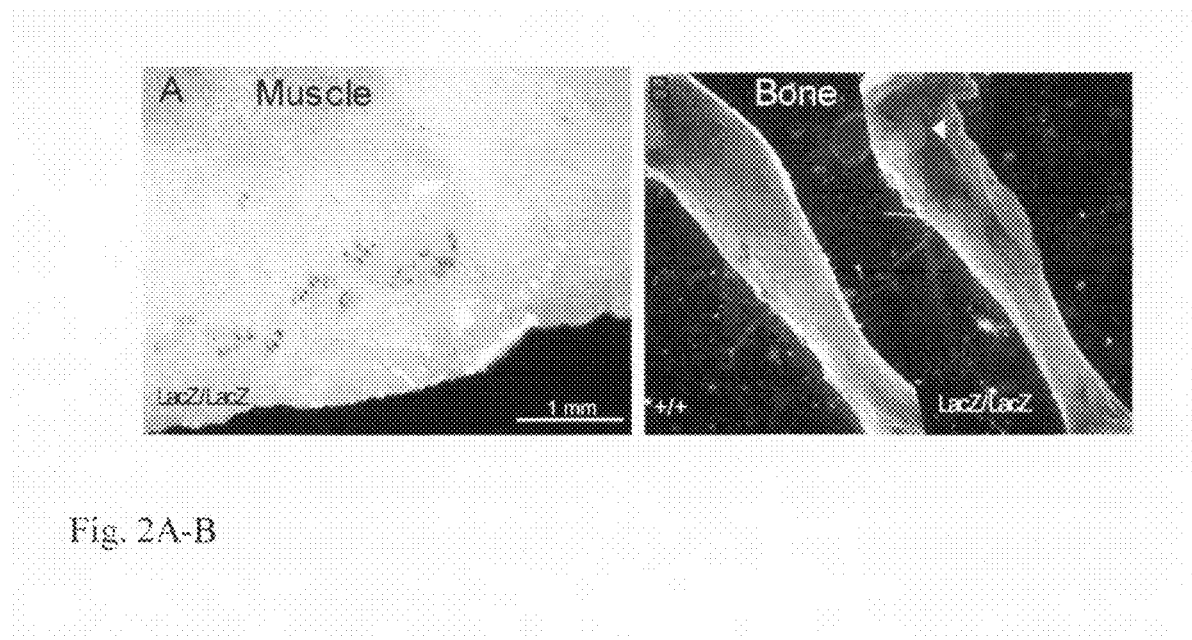
Fig. 2A-B

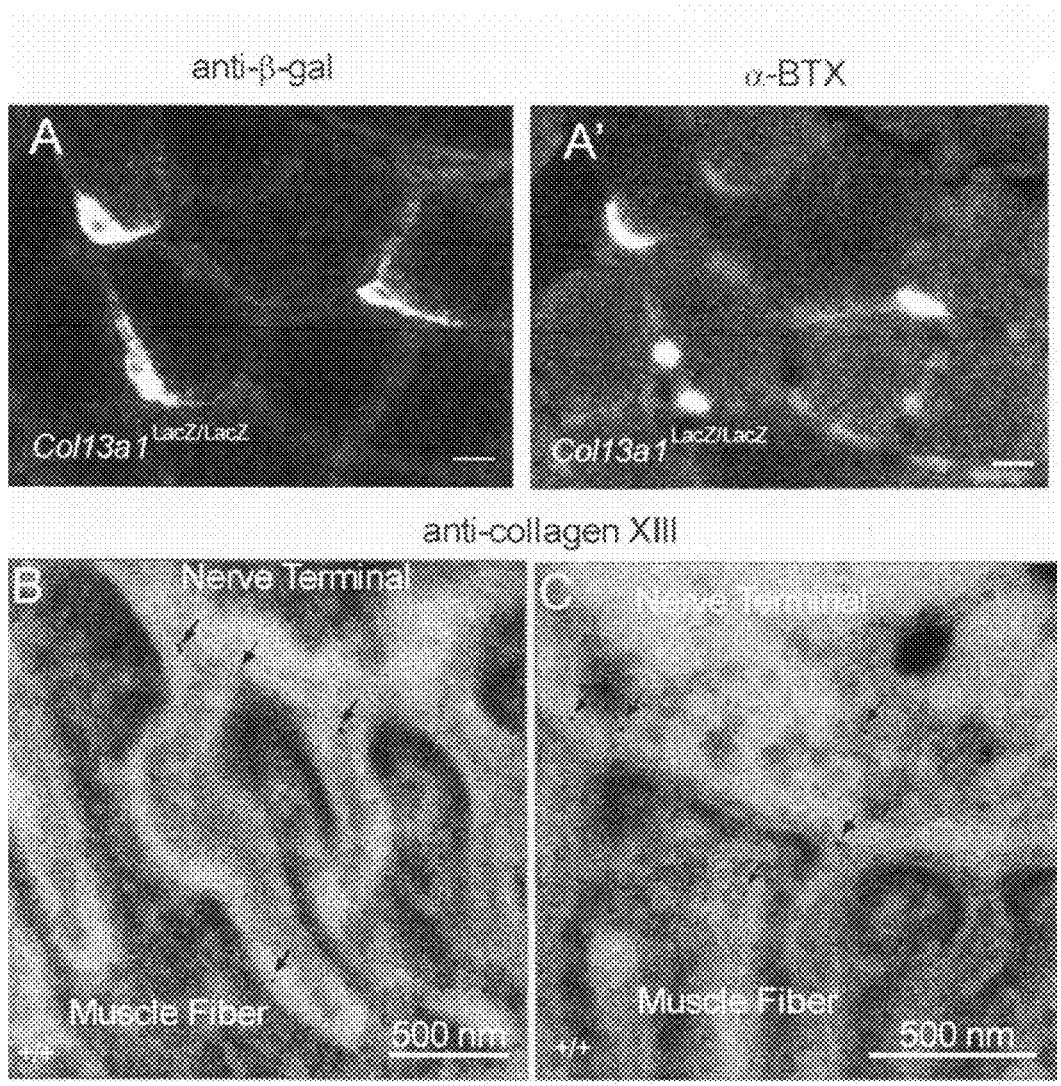
Fig. 3A-C

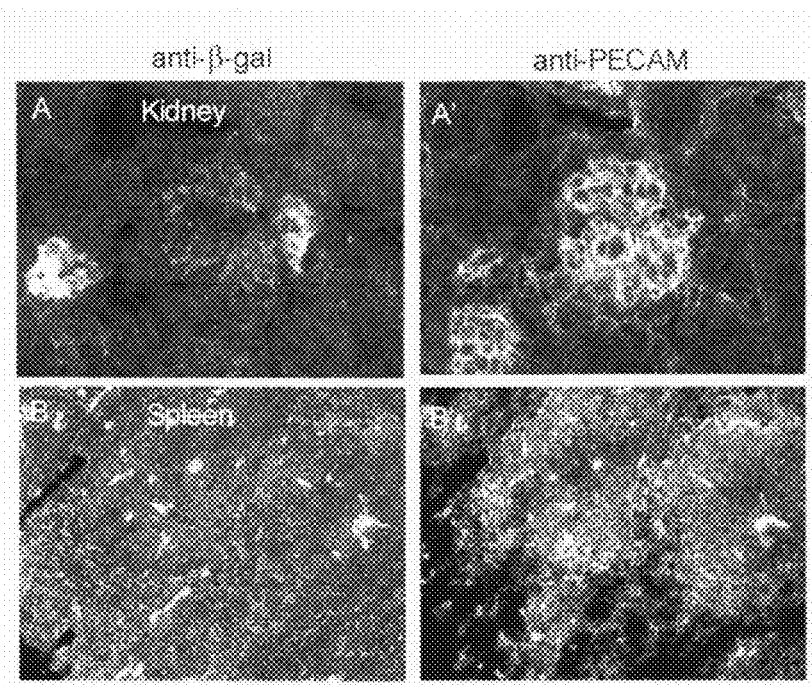
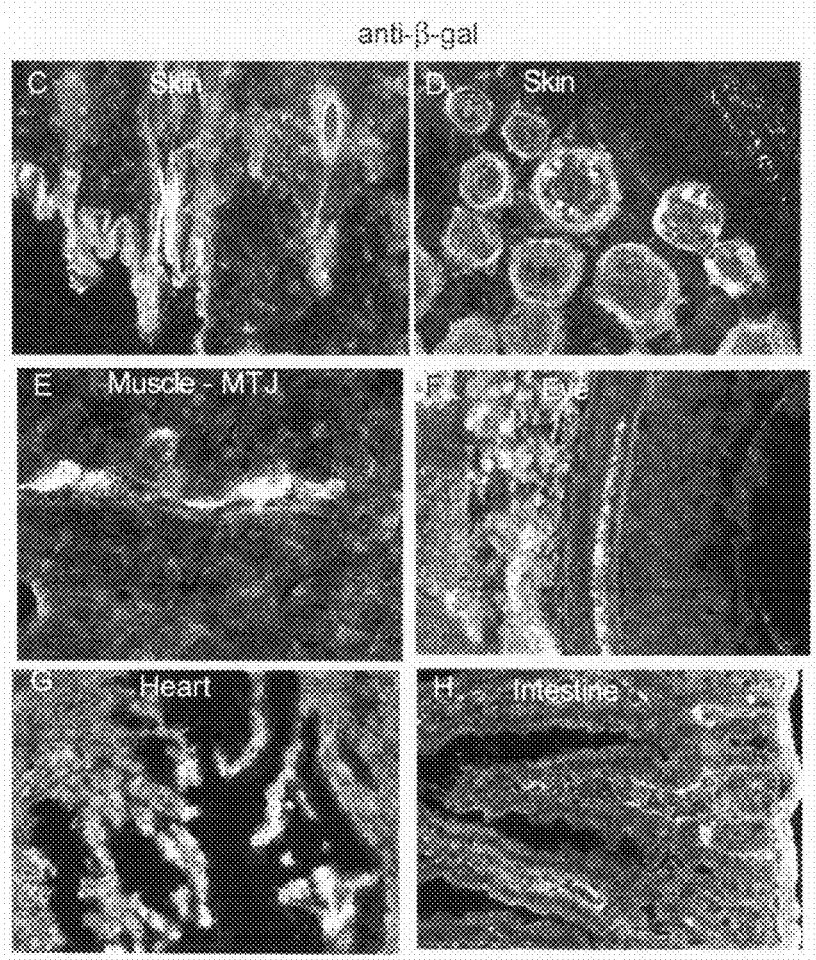
Fig 4 A-H

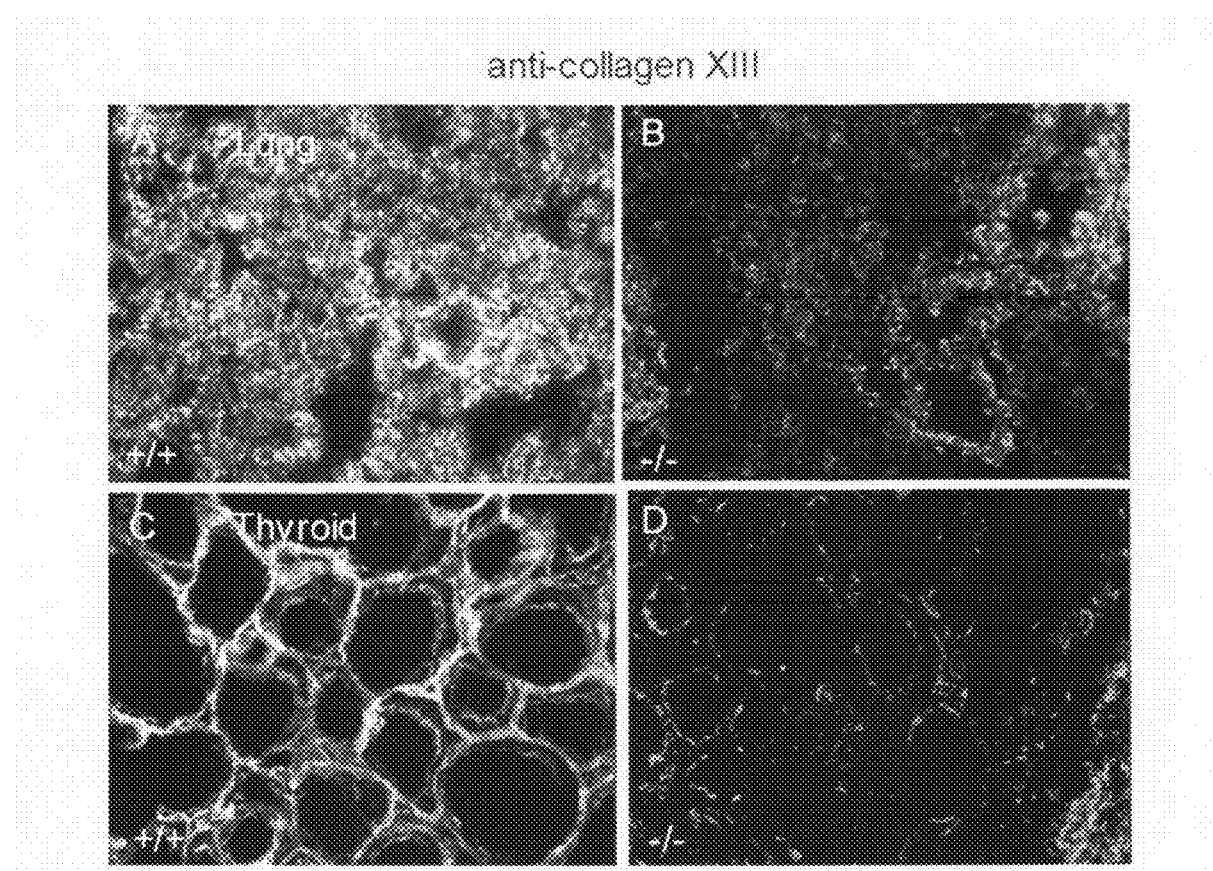
Fig. 5A-D

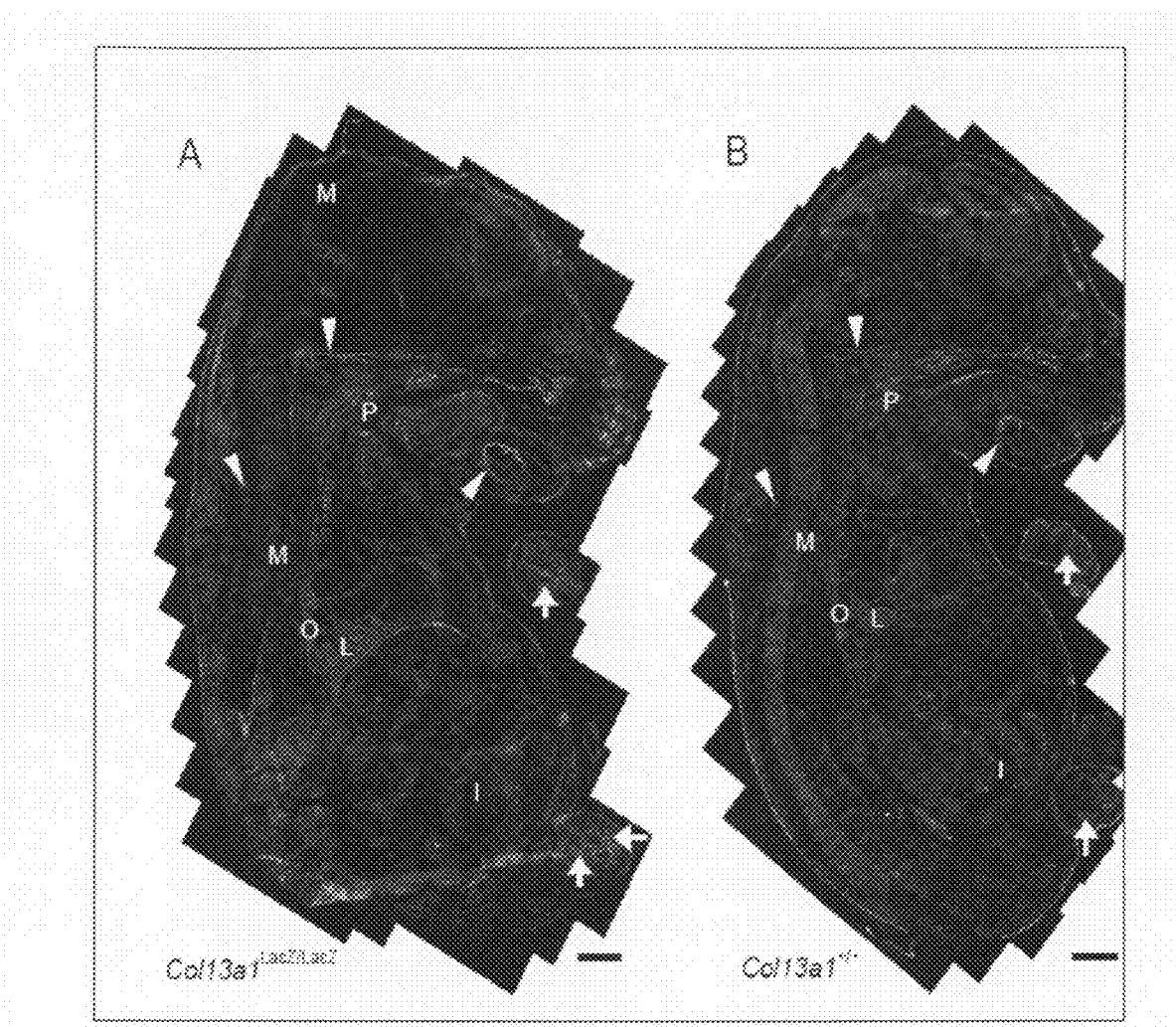
FIG. 6A-B

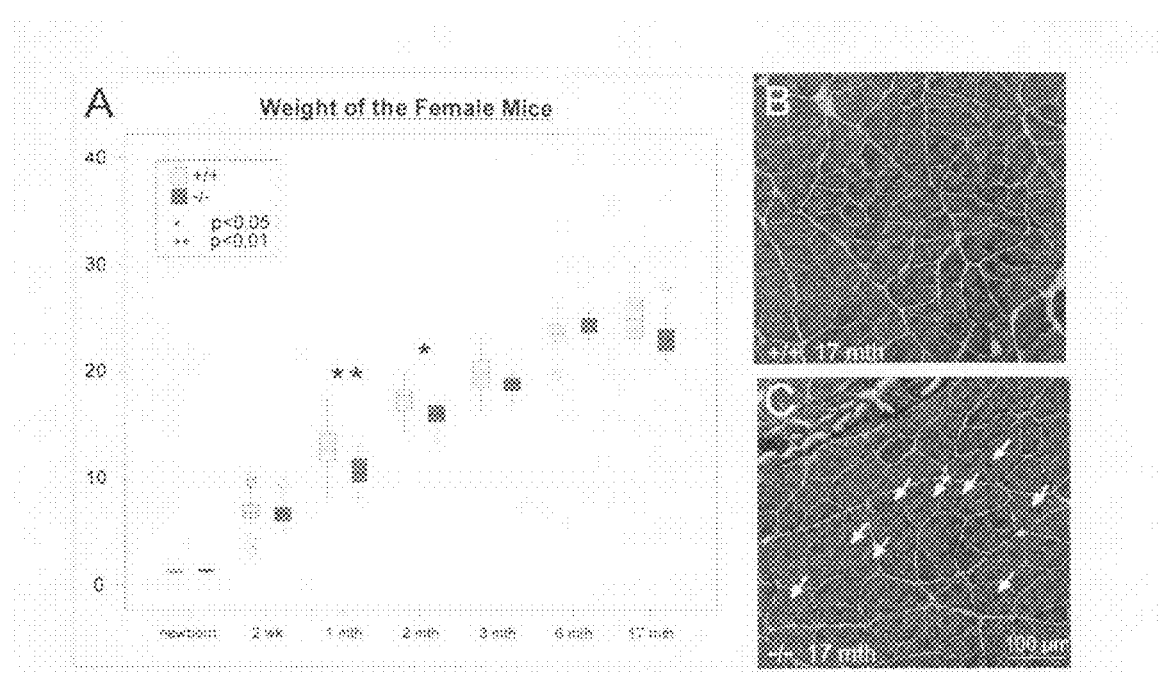
Fig. 7 A to C

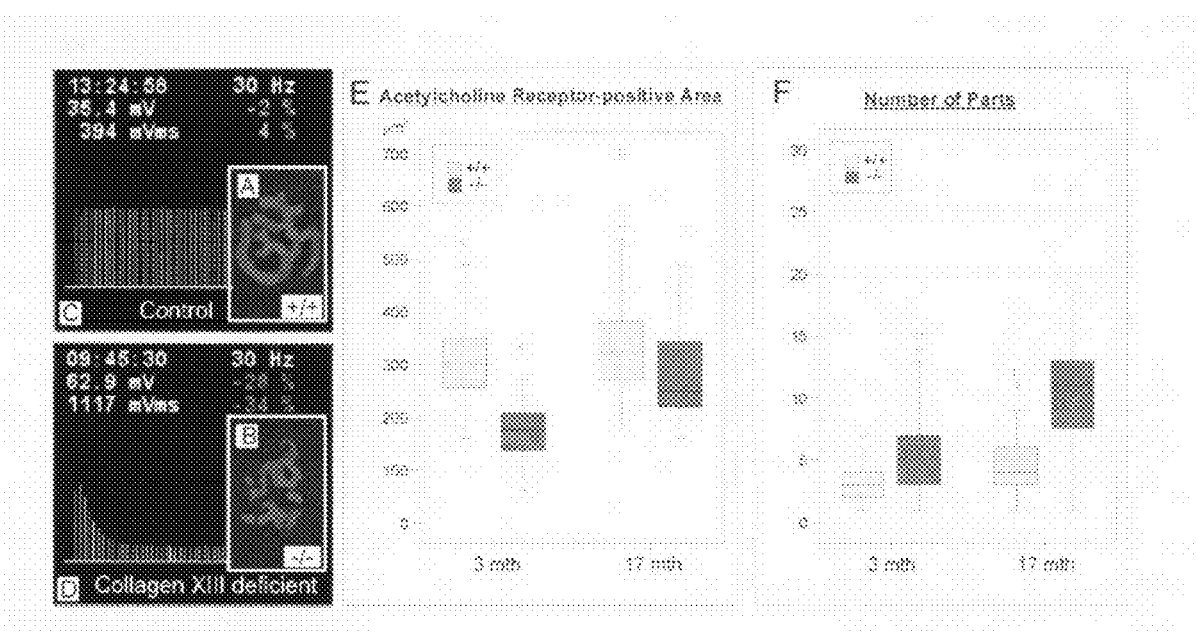
Fig. 8 A to F

METHOD FOR DIAGNOSING DISEASES

PRIORITY

This application claims priority of the U.S. provisional patent application No. 60/918,103, which was filed on Mar. 15, 2007.

FIELD OF THE INVENTION

The present invention relates to a diagnosis method of various diseases, in particular autoimmune and genetic diseases. More specifically, the present invention relates to diseases affecting tissues of organs selected from the group of spleen, brain, kidney, lung, thyroid, eye, skin, intestine, liver, pancreas, adrenal gland, prostate and heart tissues or tissues of muscles and bones. More specifically, the present invention relates to an in vitro method for diagnosing diseases affecting tissues of neuromuscular junction, in particular myasthenia gravis.

DESCRIPTION OF RELATED ART

Myasthenia gravis (MG) is a diverse autoimmune disease of neuromuscular junctions (NMJ). The disease is characterized by weakness of the skeletal muscles of the body.

In the myasthenia gravis disease (www.ninds.nih.gov/disorders/myasthenia_gravis/detail_myasthenia_gravis.htm -toc) the transmission of nerve impulses to muscle contraction is defective. Normally, acetylcholine is released from the nerve endings to the synaptic cleft when impulses travel down the nerve. Acetylcholine binds at the postsynaptic site to acetylcholine receptors which are activated resulting in a muscle contraction. In most cases of myastenia gravis disease antibodies are found against acetylcholine receptor (ACHR) and in some cases against Muscle specific kinase (MuSK), which is a receptor tyrosine kinase. The antibodies against acetylcholine receptor block, alter, or destroy the receptors for acetylcholine at the neuromuscular junction which prevents the muscle contraction from occurring. These antibodies are produced by the body's own immune system. Therefore MG is classified as an autoimmune disease. Congenital myasthenic syndrome is a genetic form of myasthenia, where mutations in the genes coding for the NMJ proteins, one of those being ACHR, have been found.

In the myasthenia gravis disease autoimmune-antibodies against the acetylcholine receptor are found in 75-80% of the cases. Patients, who don't have auto-antibodies against acetylcholine receptors, are classified as "seronegative". Hence, the diagnosis of part of the patients remains unclear despite of clear symptoms. This non-identification of disease-causing autoimmune-antibodies also prevents follow-up and prognosis. Better classification of the molecular characteristics of the disease would affect choice of various therapies.

There is thus a clear need for better method for diagnosing the myasthenia gravis disease. Since the diagnosis of other autoimmune diseases, such as Graves disease, rheumatoid arthritis (RA) and Hashimoto's thyroiditis remain sometimes unconfirmed, there is a clear need for improved diagnostic methods also for other autoimmune or genetic diseases.

SUMMARY OF THE INVENTION

It is an aim of the present invention to solve at least some problems of the prior art. In particular, it is an aim of the present invention to provide an improved method for diagnosing various autoimmune or genetic diseases.

The present invention is based on the finding of the inventors that type XIII collagen protein is highly expressed postsynaptically at the neuromuscular junction. Genetically modified mouse lines were generated in order to study the exact location and biological function of type XIII collagen. Type XIII collagen seemed to function in the maintenance of the NMJ structure. Structural changes lead to an electrophysiologically measurable decrement in nerve signal response of muscle. Similar changes in electromyography are seen in human patients with myasthenia gravis. Based on the abnormality in the neuromuscular junction of the type XIII collagen-deficient mice, the inventors concluded that the function of type XIII collagen protein may be inactivated by autoimmune antibodies in the MG patients or that there may be genetic defects of type XIII collagen gene in MG or in a genetic myasthenia. In the present invention it was shown that antibodies against type XIII collagen protein can be detected in the serum and/or plasma of a patient having myasthenia gravis symptoms.

It is an object of the present invention to provide an improved method for diagnosing autoimmune or genetic diseases, in particular diseases affecting the tissues of organs selected from the group of spleen, brain, heart, kidney, thyroid, eye, skin, intestine, liver, pancreas, adrenal gland, prostate and lungs or from the tissues selected from the group of muscles and bones or other tissues. More specifically, it is an object of the present invention to provide an improved method for diagnosing diseases affecting neuromuscular junctions.

Furthermore, it is an object of the present invention to provide an improved method for diagnosing diseases, in particular autoimmune diseases, affecting the parenchymatous cells in various tissues.

Furthermore, it is an object of the present invention to provide an improved method for diagnosing autoimmune or genetic diseases selected from the group of Graves disease, rheumatoid arthritis (RA), Hashimoto's thyroiditis and myasthenia gravis disease. More specifically, it is an aim of this invention to provide an improved method for diagnosing the myasthenia gravis disease.

It is also an object of the present invention to provide an in vitro method for diagnosing autoimmune or genetic diseases. The diagnosis can be carried out by using a biological sample, typically a body fluid sample, such as saliva, serum and/or plasma sample, outside the body of the patient.

In particular, the present invention utilizes purified recombinantly produced type XIII collagen protein.

According to one preferred embodiment of the invention type XIII collagen protein or parts of said protein is used to fish autoimmune-antibodies against the type XIII collagen protein or parts thereof in a biological sample from the patient, typically from body fluid samples, such as saliva, serum or plasma samples. The protein can be for example immobilized onto a solid surface and this test structure used to detect autoimmune-antibodies against type XIII collagen in patient samples. The test may comprise a positive and/or a negative control, said positive control being an antibody of type XIII collagen, preferably monoclonal antibody, and said negative control being for example a healthy biological sample pool, typically a healthy body fluid pool, such as a healthy serum and/or plasma pool.

Detection of positive binding can be based on ELISA or some other suitable biochemical detection method. In addition to qualitative detection, the method preferably enables quantitative detection of disease causing autoimmune-antibodies.

By a part of type XIII collagen protein is here meant an amino acid sequence lacking at least one amino acid of the full length sequence. The length of said part is preferably at least 10, more preferably at least 50, still more preferably at least 100 consecutive amino acids. Preferably, a part of type XIII collagen protein is a part capable of binding the autoimmune-antibodies formed against the type XIII collagen protein or parts thereof. More preferably, a part comprises an epitope against which the autoimmune-antibodies of a patient have been formed.

Since the abnormalities found at the neuromuscular junction can be caused by genetic defects of the type XIII collagen gene of the MG patients or in condition of genetic myasthenia, another method for diagnosing MG would be to study the nucleic acid sequence encoding the type XIII collagen.

Hence, according to another preferred embodiment of the invention the genetic data of nucleic acid sequence encoding the type XIII collagen is used to study whether there are any genetic changes in the sequence encoding the type XIII collagen in a biological sample from a patient. The biological sample may be a sample comprising nucleic acid, such as saliva or whole blood sample. The nucleic acid sequence encoding the human type XIII collagen protein with various transcription variants, nucleic acid sequence of exons and genomic sequenses are found at the National Center for Biotechnology Information (http://www.ncbi.nlm.nih.gov/ with the accession numbers NW_001837986, NW_924796, NT_008583, AL138925, NM_080814, AJ293624, AF071009, AH002721, M69008, M69009, M69001, M69002, M69003, M69004, M69005, M69006, M69007, M69010, M69000, M68997, M68996, M68995, M68994, M68993, M68992, M68991, M68987, M68986, M68985, M68984, M68983, M68982, M68981, M68990, M68980, M68989, M68988, M68979, M68978, M68977, M68976, M68975, M68974, M81618, M81617, M68999, M68998, AH002648, M20803, M20804, M20797, M20798, M20799, M20800, M20801, M20802, M20805, M20795, M59217).

According to the present invention screening of type XIII collagen autoimmune-antibodies or genetic changes in the nucleic acid sequence encoding the type XIII collagen protein can be used to diagnose autoimmune and genetic diseases. In particular, these methods can be used to diagnose or classify diverse and overlapping autoimmune or genetic diseases. Typically, the present invention can be used to diagnose myasthenia gravis, in particular acetylcholine receptor "seronegative" myasthenia gravis.

In conclusion the methods and products of the present invention can be used to diagnose any autoimmune or genetic diseases affecting the tissues of organs selected from the group of spleen, brain, heart, kidney, thyroid, eye, skin, intestine, liver, pancreas, adrenal gland, prostate and lungs or tissues of muscles or bones or other tissues, where type XIII collagen protein expresses in high levels.

Considerable advantages are achieved by means of the present invention.

As mentioned above, in the autoimmune disease myasthenia gravis part of the patients are classified as "seronegative" since they don't have autoimmune-antibodies against the classical antigen, acetylcholine receptor, which are found only in 75-80% of the cases.

Thus, the diagnosis of the seronegative MG patients remains unclear despite of clear symptoms. This non-identification of disease-causing autoimmune-antibodies also prevents follow-up and prognosis. It is to be expected that better classification of the molecular characteristics of the disease affects choice of therapies.

The methods of the present invention also provide tools to reorganize the classification, diagnosis, follow-up and prognosis of autoimmune or genetic diseases with overlapping and mixed symptoms. The method can be applied on any autoimmune or genetic disease and it enables recognition of type XIII collagen autoimmune-antibodies in diseases yet not known to bear such antigens or recognition of patients carrying genetic changes in the nucleic acid sequence encoding type XIII collagen in diseases yet not known to bear such genetic changes.

This method thus aids in diagnosis, follow-up and prognosis and selection of the most suitable therapy of any disease positive for type XIII collagen autoimmune-antibodies or caused by genetic changes in the nucleic acid sequence encoding type XIII collagen.

Genetic changes in nucleic acid sequence encoding the type XIII collagen protein, i.e. mutations in the type XIII collagen gene locating in the exons, introns or regulatory regions, can lead to either lack, haplo-insufficiency or some other miss-expression of the type XIII collagen protein. Detecting mutations in the type XIII collagen gene can be used to diagnose any human genetic disease due to miss-expression of the type XIII collagen protein. Knowing the exact mutations further aids in designing a cure for the genetic diseases. Testing may be performed by extracting nucleic acid, for example DNA from a biological sample, such as from a body fluid sample, for example from saliva or blood sample, and amplification of the nucleic acid by for example PCR followed by nucleotide sequencing using for example gene-specific oligonucleotide primers in the amplification and sequencing.

By a part of a nucleic acid sequence encoding type XIII collagen is meant a part of the full length nucleic acid sequence lacking at least one nucleic acid of the full-length sequence. Preferably, the part is a consecutive sequence of nucleic acids the length of which is at least 60%, more preferably at least 70%, still more preferably at least 80%, still more preferably at least 90% of the full length sequence. Preferably, the part is capable of encoding type XIII collagen. Alternatively, by a part is meant a part for which an oligonucleotide is specific or has been specifically designed.

Next the invention will be examined more closely with the aid of the following detailed description in which reference is made to the appended drawings.

BRIEF DESCRIPTION OF THE DRAWINGS

FIG. 1A-M describe generation of type XIII collagen targeted mouse lines.

FIGS. 2A and B describe β-galactosidase stainings of adult mouse tissues from the Col13a1$^{LacZ/LacZ}$ mice indicating the locations where type XIII collagen can be found at highest concentrations (white arrow).

FIG. 3A shows type XIII collagen in muscle from the Col13a1$^{LacZ/LacZ}$ mouse line stained for β-galactosidase to locate at the neuromuscular junction. Wild-type neuromuscular junctions were stained for type XIII collagen in immunoelectron microscopy (B-C).

FIG. 4A to H show anti-β-galactosidase antibody stainings of adult mouse tissues indicating the locations where type XIII collagen is expressed at low or moderate local concentrations.

FIG. 5A to D show anti-type XIII collagen antibody stainings of selected additional adult mouse tissues from wild-type and knock-out mice.

FIGS. 6A describes an anti-β-galactosidase antibody staining of Col13a1$^{LacZ/LacZ}$ mouse fetal tissues and 6B anti-type XIII collagen antibody staining of wild-type mouse fetal tissues.

FIG. 7A to C describe the consequences of the lack of type XIII collagen in mice.

FIG. 8A to F show type XIII collagen as a distinguished component of the neuromuscular junction.

DETAILED DESCRIPTION OF THE INVENTION

Definitions

Figure 9:
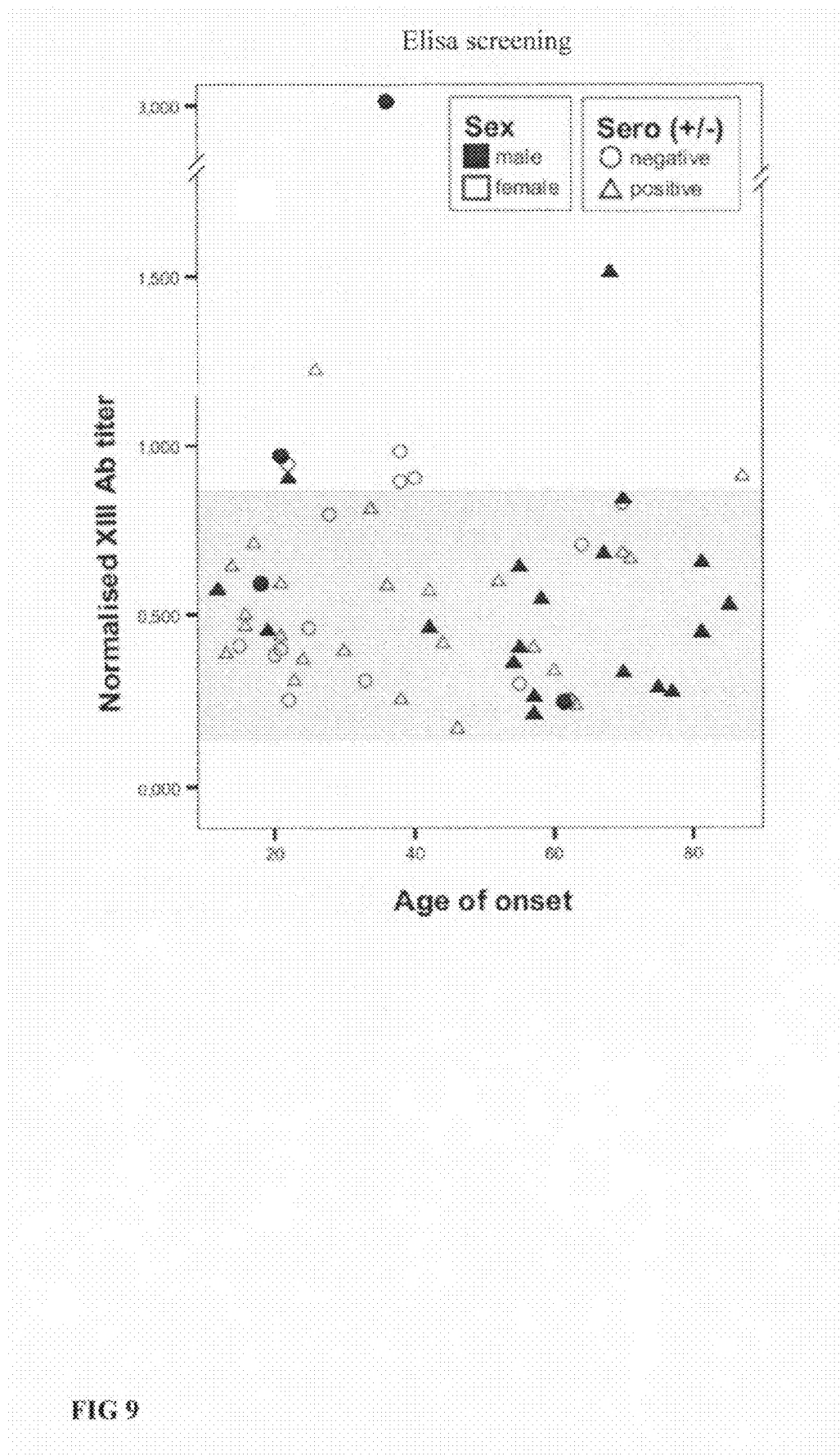
FIG. 9 shows anti-type XIII collagen autoimmune-antibodies in patients' sera using ELISA screening.

In "autoimmune diseases" an organism cannot recognize its own constituent parts as its own parts. This results in an immune response against its own cells and tissues. According to the present invention type XIII collagen can be used to diagnose autoimmune diseases affecting various tissues comprising tissues in spleen, brain, kidney, heart, thyroid, eye, skin, intestine, liver, pancreas, adrenal gland, prostate and lungs or in bones, muscles or other tissues. In particular, the present invention can be used to diagnose autoimmune diseases affecting the neuromuscular junctions. The autoimmune diseases may be selected preferably from the group comprising myasthenia gravis, rheumatoid arthritis (RA), Graves disease and Hashimoto's thyroiditis. DeBellis et al. 2005 have shown type XIII collagen antibodies in sera of Graves' disease patients with active ophthalmopathy. Anti-type XIII collagen antibodies was believed to reflect an increased expression of type XIII collagen on the membrane of activated fibroblasts in the patients.

More specifically, the present invention can be used to diagnose autoimmune diseases affecting parenchymatous cells in various tissues of various organs.

By "genetic disease" is here meant a disease resulting from genetic changes in a gene or genes of a patient. Genetic diseases comprise for example hereditary diseases.

Tissues where type XIII collagen may be involved in disease processes include the muscles, the bones, the heart and malignant processes. In muscle, highest expression of type XIII collagen localizes at the neuromuscular junctions and in bone in the periosteum. Other tissues where type XIII collagen may be involved in disease processes include spleen, brain, kidney, thyroid, eye, skin, intestine, liver, pancreas, adrenal gland, prostate and lungs.

An in vitro method means that the method does not comprise any step which is carried out within a body or cell of an organism.

"A biological sample" means in this invention any biological sample from a mammalian body, in particular human body. Typically, a biological sample means a body fluid sample. The sample may comprise urine, saliva, and blood, parts of blood, such as serum or plasma. Preferably the body fluid sample is a serum sample.

Testing for genetic changes in a gene is performed by extracting DNA from for example a blood or saliva sample from the patient, amplifying the DNA by for example PCR amplification method and sequencing the nucleotide sequence. Gene-specific oligonucleotide primers may be used in the amplification and sequencing.

Type XIII collagen is a type II oriented transmembrane protein with a short cytosolic domain and mainly collagenous ectodomain (Hägg et al. 1998). Cell culture studies have shown its involvement in cell adhesion. In earlier studies it has been found in tissues in various junctional structures (Hägg et al. 2001). Tu et al. (2002) describes the production, purification and characterization of recombinant type XIII collagen.

"Determining the presence or absence of autoimmune-antibodies against type XIII collagen" means that a clear difference in the amount of autoimmune-antibodies against type XIII collagen is found in the sample from the patient compared to a control pool. The amount of autoimmune-antibodies against type XIII collagen in the sample of a patient can be at least 10% higher, preferably at least 20% higher, more preferably at last 30% higher than in the sample of a control pool.

"A control pool" means a mixture of persons having no symptoms of the disease to be diagnosed by the method.

By an "ELISA method" is meant an enzyme-linked immunosorbent assay, where type XIII collagen protein is used to detect autoimmune-antibodies present in a patient's body fluid sample. The result is compared with a result where the body fluid is from a pool of healthy persons not having any symptoms of the disease to be diagnosed. In the ELISA method purified type XIII collagen protein is preferably immobilized onto a solid surface to fish autoimmune-antibodies against the type XIII collagen protein.

As is known to a person skilled in the art also other immunoassays except ELISA can be used in the assays of this invention. For example DELFIA, where the principle is the same as in ELISA, but the detection is not enzyme based.

The term "purified" denotes here that the indicated molecules are present in the substantial absence of other biological macromolecules, such as proteins, polynucleotides and the like. The term "purified" means preferably at least 95% by weight, more preferably at least 99.8% by weight, of the indicated biological macromolecules present (but water, buffers, and other small molecules, especially molecules having a molecular weight of less than 1000 daltons can be present). The term "isolated" refers to a protein molecule separated not only from other proteins that are present in the natural source of the protein, but also from other proteins, and preferably refers to a protein found in the presence of (if anything) only a solvent, buffer, ion, or other component normally present in a solution of the same. The terms "isolated" and "purified" do not encompass proteins present in their natural source.

Purified collagens for use in the methods of the invention may be isolated from human tissues, but preferably they may be produced by recombinant DNA technology. A description of how to produce type XIII collagen by recombinant DNA technology can be found, for example in international patent publications WO 93/07889 and WO094/16570, and Tu et al., 2002. Preferably, human type XIII collagen produced by recombinant DNA technology can be used in the methods and kits of this invention.

Using a genetically modified mouse lines the inventors have shown that the main type XIII collagen location in a living organism is the neuromuscular junction, and that deficiency of the protein results in defective structural integrity and function of this cell-cell junction. By another mouse line the type XIII collagen protein has been shown to participate in regulation of normal immunity thus suggesting that type XIII collagen is likely to be involved in a broader spectrum of immunological syndromes. To mention some more human diseases, Hashimoto thyroiditis and common variable immunodeficiency, could be added to the list of candidate diseases with the involvement of type XIII collagen since symptoms in these diseases are in line with the ones found in type XIII collagen transgenic mice or symptoms are found in such tissues that express type XIII collagen. In addition, blood counts show an altered white blood cell profile in the type XIII collagen transgenic mice further suggesting its involvement in the control of immune system.

The main target of autoimmune-antibodies in myasthenia gravis is the protein acetylcholine receptor. However, 20-25% of the patients are negative for these antibodies and the diagnosis remains unclear despite of clear symptoms. Type XIII collagen is a novel target of autoimmune-antibodies in this disease and identification of such antibodies can be expected to help in the diagnosis of myasthenia gravis, and later in follow-up and prognosis. Further, identification of autoimmune-antibodies against type XIII collagen could clarify definition and diagnosis in a spectrum of mixed and overlapping immune syndromes. Due to its expression at the neuromuscular junctions and at a lower level in myotendinous junctions, type XIII collagen may also be involved in other muscle disorders.

Type XIII collagen gene mutations have not thus far been found in any human disease. The present results with transgenic mice have given a lot of information on the expression-pattern and symptoms resulting from the deficiency or miss-expression of this protein. This enables limiting the selection of human diseases where it would be sensible to search type XIII collagen gene mutations. Phenotypical changes in type XIII collagen transgenic mice are significant indicating that there has to be human diseases with mutations in the type XIII collagen gene, although yet unidentified.

The present invention is based on studies where two targeted mouse lines were generated; 1) a LacZ reporter line to study the exact location and 2) a null line lacking any type XIII collagen expression to study biological function of the transmembrane type XIII collagen, also found as a shed, soluble protein.

β-galactosidase marker stainings showed that type XIII collagen is highly expressed postsynaptically at the neuromuscular junction. The endplate structure in homozygous mice in both lines lacking intact type XIII collagen was smaller and more fragmented than that seen in controls. These structural changes were accompanied by an electrophysiologically measurable defect in a nerve conduction study. Structural and functional defects of the NMJ had impact on the weight, behaviour and general condition of the mice. The mice developed myopathy at old age, but yet the structure of NMJs was more disturbed in young than in old mice. These studies thus indicated that type XIII collagen contributes to the stabilization of the NMJ structure.

Collagen can be found in most tissues, the ones mentioned above are not the only ones. If further searches were carried out in an organism, additional interesting locations would certainly be identified. Collagen localizes in many tissues in very restricted, specified structures, and only in some tissues, like in lung, it can be found broadly. Although concentrating in specific structures, it is hard to conclude the functional mechanism of this protein. Type XIII collagen is expressed in some of such structures that one could imagine it functioning as an adhesive protein (like the NMJ and myotendious junction, MTJ). As a transmembrane protein, this may very well be the case. Transmembrane type XIII collagen has been shown to be essential for maintaining the muscle integrity (Kvist et al., 2001). Some of its locations also indicate that it might be involved in mechano-sensory systems (periosteum, juxtaglomerular cells), as already suggested in the context of bone (Ylönen et al., 2005, Ylönen 2005). Nevertheless, type XIII collagen most likely harbours some more complicated functions than only structural ones. Type XIII collagen as a target of autoimmune-antibodies may result in a wide variety of symptoms. A summary of the tissue distribution of type XIII collagen can be found in Table I.

TABLE I

A summary of the type XIII collagen tissue distribution found either in adult or fetal tissues, originating either from human or mouse species, the data obtained either by immunostaining, in situ hybridization or Western blotting according to the text or references.

| Tissue | Human | Mouse | Adult | Fetal | Reference |
|---|---|---|---|---|---|
| Muscle | x | x | x |   | (Hägg et al., 2001) |
| Muscle |   | x |   | x | (Sund et al., 2001) |
| Muscle - NMJ postsynaptic |   | x | x |   | present invention |
| Bone and cartilage | x |   |   | x | (Sandberg et al., 1989) |
| Bone and cartilage |   | x |   | x | (Sund et al., 2001) |
| Bone and cartilage |   | x | x | x | (Ylönen et al., 2005) |
| Bone - highest at puberty |   | x | x |   | present invention |
| Kidney |   | x | x |   | present invention |
| Spleen |   | x | x |   | present invention |
| Skin | x |   | x |   | (Peltonen et al., 1999) |
| Skin | x |   |   | x | (Sandberg et al., 1989) |
| Skin |   | x |   | x | (Sund et al., 2001) |
| Eye | x |   | x | x | (Sandberg-Lall et al., 2000) |
| Eye |   | x | x | x | present invention |
| Heart |   | x | x |   | (Hägg et al., 2001) |
| Heart |   | x |   | x | (Sund et al., 2001) |
| Heart - valve |   | x | x | x | present invention |
| Intestine |   | x | x |   | (Hägg et al., 2001) |
| Intestine |   | x |   | x | (Sund et al., 2001) |
| Lung |   | x | x |   | present invention |
| Lung |   | x |   | x | (Sund et al., 2001) (Hägg et al., 2001) |
| Brain |   | x | x |   | present invention |
| Brain |   | x |   | x | (Sund et al., 2001) |
| Peripheral nerves |   | x | x |   | (Hägg et al., 2001) |
| Peripheral nerves |   | x |   | x | (Sund et al., 2001) |
| Thyroid |   | x | x |   | present invention |
| Arterial wall |   | x | x |   | (Hägg et al., 2001) |
| Testis |   | x | x |   | (Hägg et al., 2001) |
| Pancreas |   | x | x |   | present invention |
| Liver |   | x | x |   | present invention |
| Epididymis |   | x | x |   | present invention |

TABLE I-continued

A summary of the type XIII collagen tissue distribution found either in adult or fetal tissues, originating either from human or mouse species, the data obtained either by immunostaining, in situ hybridization or Western blotting according to the text or references.

| Tissue | Human | Mouse | Adult | Fetal | Reference |
|---|---|---|---|---|---|
| Salivary gland | | x | x | | present invention |
| Adrenal gland | | x | x | | present invention |
| Prostate | | x | x | | present invention |
| Vas deferens | | x | x | | present invention |

Human, Fetal and Adult Expression Data

The data in Table I is derived from the present invention and a collection from prior art publications. In the prior art in which type XIII collagen knock-out mice were not available antibody stainings with anti-type XIII collagen antibodies could not be controlled with tissue samples lacking type XIII collagen but they were performed with the best available controls. Nowadays we know that our anti-type XIII collagen antibodies, present and past, have some non-specificity. For that reason, published antibody stainings can in some occasions give a bit too positive impression of the expression pattern of type XIII collagen in mice. The same holds with the results on expression obtained with in situ hybridization of mouse tissues. Naturally, it is not even possible to control human tissue stainings in such a way at all.

Type XIII collagen occurs in focal adhesions of cultured cells and in tissues at many sites of cell-matrix contact and at some cell-cell contacts, and it is thus thought to have a role in cellular adhesion. Type XIII collagen expression has been found in all tissues studied but in relatively small amounts. By antibody stainings, type XIII collagen has been localized to the adhesive structures between cells and matrix but also between cells. Intercalated discs of the myocardium in mouse (Hägg et al., 2001) and human keratinocytes of the skin epidermis (Peltonen et al., 1999) are examples of cell-cell contacts where type XIII collagen is present. In mouse striated muscle, myotendinous junctions and costameres represent cell-matrix contact sites where type XIII collagen can be found. In muscle, type XIII collagen expression is also reported at neuromuscular junctions, possibly at the Schwann cells that cap the nerve terminal, as well as sarcolemma and peripheral nerves. Note that type XIII collagen staining did not coincide with α-BTX used as a control here in FIG. 3, and therefore we considered the signal described in the previous sentence to locate at the Schwann cells surrounding the NMJ. By antibody stainings, the type XIII collagen protein has been localized on the basal side of various epithelia but also in mesenchyme and capillaries (Hägg et al., 2001). In the eye, the strongest signals were seen in in situ hybridizations and immunofluorescence stainings in the optic nerve bundles and in the ganglion cell layer of the retina. Other notable locations containing type XIII collagen included the developing ciliary smooth muscle, the posterior two-thirds of the corneal stroma and the striated extraocular muscles (Sandberg-Lall et al., 2000). In development, human type XIII collagen has been located by in situ hybridization to the reticulin network of calvarial bones and, to some extent, the periosteum. In long bones, type XIII collagen localizes both in cartilage and in ossifying bone. The hypertrophic and proliferating chondrocytes of the growth plate as well as the chondrocytes of the perichondrium and articular surfaces express type XIII collagen. In ossifying long bone, type XIII collagen is found in the reticular network between spicules and periosteum, as it was also shown for calvarial bones (Sandberg et al., 1989). In addition, type XIII collagen mRNA was found by in situ hybridization in the early human placenta (Juvonen et al., 1993). In mouse development, type XIII collagen has been found to be expressed not only by the cells mentioned above, but also by neurons of the central and peripheral nervous system (Sund et al., 2001). In summary, type XIII collagen is expressed by cells of both epithelial and mesenchymal origin.

The following non-limiting examples illustrate the invention:

EXAMPLE 1

Generation of the Type XIII Collagen Mouse Lines and the Expression Pattern of the Type XIII Collagen Protein Generation of the Knock-Out Mouse Line Generation of the knock-out vector was initiated by cloning a 9-kb genomic BamHI fragment (FIG. 1A) including the predicted promoter area, 5' UTR sequences, and the first protein-coding exon (Kvist et al., 1999). A 2.3-kb sequence including the promoter and the first exon was released from the resultant plasmid and replaced by the neomycin resistance gene (neo$^r$) with the phosphoglycerate kinase (PGK) promoter and the polyA signal released from the plasmid pBSloxP-neor-HSV-tk-loxP (Potocnik et al., 2000). Stop codons in all three frames were added downstream from the cassette. The targeting vector (FIG. 1B) was linearized, and 20 μg of it was electroporated into R1 embryonic stem (ES) cells (Nagy et al., 1993). The ES cells were cultured overnight, after which they were subjected to G418 sulphate selection for 6-7 days. Individual colonies were picked, cultured, stored, and DNA was analyzed for homologous recombination by restriction enzyme digestion and Southern blot hybridization with internal (data not shown) and external probes, as illustrated in FIG. 1D.

ES cells from one targeted clone were used to generate a targeted knock-out mouse line (Col13a1$^{T/T}$, FIGS. 1B and E). Cells were injected into C57BL/6J blastocysts, which were then implanted into pseudopregnant foster mothers. Several resultant highly chimeric mice were bred with C57Bl/6J females to establish a mouse line with an inbred genetic background. Col13a1$^{T/T}$ males were bred with C57Bl/6J females, which retain Cre recombinase activity in mature oocytes irrespective of Cre transgene transmission (Sakai and Miyazaki, 1997) to accomplish loxP-neo$^r$-loxP cassette removal and to attain a Col13a1$^-$ mouse line (FIG. 1C). The genomic rearrangement was certified by southern blot hybridization, as shown in FIG. 1F-G.

Generation of the β-Galactosidase Reporter Mouse Line

The 7.4-kb BamHI genomic restriction fragment (FIG. 1H) containing exon 2 and the surrounding intron sequences was cloned. The 1.2-kb fragment including most of the exon 2 coding sequences and the beginning of the second intron was released and replaced by the LacZ-neo$^r$ cassette in-frame with type XIII collagen sequences at the same time destroying the furin endoprotease recognition sequence. The targeting vector was linearized, and 25 μg was used for electroporation to generate a Col13a1$^{LacZ}$ allele (FIG. 1I, K) in the Transgenic Core Facility of Biocenter Oulu according to standard methods. Cells from two separate clones were used to generate reporter mouse lines (Col13a1$^{LacZ/LacZ}$, FIG. 1L). Cells were injected into C57BL/6J blastocysts, which were then implanted into pseudopregnant foster mothers. Several resultant highly chimeric mice were bred with C57Bl/6J females to establish mouse lines with an inbred genetic background.

Demonstrating Mouse Lines Deficient of Type XIII Collagen 16.5 dpc fetuses from homozygous Col13a1$^{-/-}$, Col13a1$^{LacZ/LacZ}$ and C57BL/6J matings were used as a source for RNA to generate cDNAs in RT-reactions. The amount of type XIII collagen transcripts was measured by quantitative real-time PCR with primer-probe-pairs from exon 2-4 and 25-26 areas. The results show a total lack or extremely low levels of type XIII collagen transcripts in both mouse lines (FIG. 1M).

FIG. 1A-M describe generation of type XIII collagen targeted mouse lines. A and H, Restriction maps of the endogenous mouse type XIII collagen gene in the first (A) and second (H) exon areas. The probes (P1-P4) used later for genotyping are indicated by grey boxes. The scale for 1 kilo base (kb) is indicated in H. The sizes of relevant restriction fragments are shown below by arrows. The abbreviations for the restriction enzymes are B; BamHI, E; EcoRI, H; HindIII, N; NarI, S; SfiI and X; XbaI. B, The type XIII collagen knock-out targeting vector, the targeted allele and the sizes of relevant restriction fragments. The loxP sites are indicated by arrowheads and the abbreviation PGK-neor stands for the neomycin resistance gene driven by phosphoglycerate kinase promoter, the direction of which is indicated by an arrow. C, Targeted knock-out allele after Cre-mediated excision of the resistance gene. D, Targeted ES cell DNAs are digested with XbaI and hybridized with the external probe 1 (P1), showing two targeted clones (+/T). E, DNA extracted from the offspring of heterozygous mating carrying the targeted allele is digested with XbaI and hybridized with an internal probe 2 (P2) showing wild-type (+/+), heterozygous (+/T) and homozygous (T/T) pups with respect to the targeted allele. F, DNA extracted from wild-type (+/+) and heterozygous targeted (+/T) mice, and from offspring of a homozygous targeted male and a Cre female digested with BamHI and hybridized with the internal probe 2 (P2), showing a pup with the resistance gene excised (+/−). G, DNA extracted from the offspring of heterozygous parents carrying a copy of the excised gene is digested with BamHI and hybridized with the internal probe 2 (P2) showing wild-type (+/+), heterozygous (+/−) and homozygous (−/−) pups. I, The type XIII collagen targeting reporter gene construct, the targeted allele, and the sizes of the relevant restriction fragments. J, The primary structure of the mouse type XIII collagen, where non-collagenous domains are indicated by black and collagenous domains by white boxes, coiled-coil motifs by striped boxes, and the membrane spanning region by a light grey box. Below this is the protein expressed in targeted reporter mice, the dark grey box indicating β-galactosidase. K, ES cell DNAs are digested with EcoRI and hybridized with the external probe 3 (P3) showing two targeted clones (+/LacZ). L, DNA extracted from the offspring of heterozygous mice carrying a copy of the reporter gene is digested with HindIII and hybridized with the internal probe 4 (P4) showing wild-type (+/+), heterozygous (+/LacZ) and homozygous (LacZ/LacZ) pups. M, The amount of type XIII collagen transcripts was measured by quantitative real-time PCR with two distinct primer pairs together with their probes, chosen from the exon 2 to 4 and the exon 25 to 26 areas. The transcript levels in 16.5 dpc wild-type fetuses from a C57BL/6J mating (dark grey column, n=4), homozygous Col13a1$^{-/-}$ (striped columns, n=5) and Col13a1$^{LacZ/LacZ}$ (white columns, n=5) matings. The results are given as artificial units, so that the value for wild-type fetuses is defined as 100%, and the others are compared to it. The results are presented as mean values, and the standard deviation is indicated.

Tissues with Highest Type XIII Collagen Expression in Adult Mice

Type XIII collagen can occur as transmembrane-bound and shed protein. The relative proportion of these two forms in tissues is not currently known. The β-galactosidase reporter in our mice indicates the cells that express type XIII collagen. Moreover, the location of β-galactosidase can be expected to mark the location of the transmembrane-bound form. The reporter can not be shed from the plasmamembrane to become a soluble protein as type XIII collagen can. Thus the location of β-galactosidase may not fully coincide with the shed type XIII collagen protein in tissues.

The mice were sacrificed, and the tissue pieces were stained utilizing β-galactosidase enzyme activity as stated (Gossler and Zachgo, 1993). Two adult tissues stained with this non-sensitive method indicating the places where type XIII collagen expression was locally high. The staining in muscle indicated neuromuscular junctions (NMJ) and the staining could be seen in adult muscle at any age (FIG. 2A). The second place where type XIII collagen was visible with this reporter method was the periosteum at sites of muscle attachment (FIG. 2B) and some endosteal cells (data not shown) of bone at the age of one month (Latvanlehto, 2004). The staining in bone could not be seen in younger or older than one month old mice indicating regulated expression at puberty during the growth phase. No staining in embryos could be detected indicating lower local concentrations of type XIII collagen during development.

In addition to these two clear and confirmed stainings, β-galactosidase enzyme staining gave some signal in whole tissue preparations in kidney and heart.

FIGS. 2A and B describe β-galactosidase stainings of adult mouse tissues from the Col13a1$^{LacZ/LacZ}$ mice indicating the locations where type XIII collagen can be found at highest concentrations. In muscle, staining localizes at the NMJs (A) and in bone in the periosteum (B).

As stated before, the β-galactosidase marker indicates the origin of the type XIII collagen protein. The reporter staining locates in muscle at the NMJ to the postsynaptic muscle cell. The cell expressing type XIII collagen is recognized by anti-β-galactosidase antibody (FIG. 3A) and comparing the staining with the postsynaptic plasmamembrane (FIG. 3A') β-galactosidase staining clearly remains at the muscle cell side of the synapse. This can be seen in immunoelectron microscopy as well (data not shown). When NMJs are stained for type XIII collagen in immunoelectron microscopy, gold particles indicating the type XIII collagen protein locates at the postsynaptic plasmamembrane as well as the adjacent basement membrane (FIG. 3B). Some particles can be also seen in the terminal nerve cell (FIG. 3C). This is not quite yet confirmed (too few negative controls thus far), but if so, the type XIII collagen protein is shed at this location from the muscle plasmamembrane and endocytosed by the nerve. Just to mention here, that ectopically added, soluble type XIII collagen protein speeds up the maturation of the junctions on cultured myoblasts indicating a biological, active role for the soluble, shed type XIII collagen.

FIG. 3 A shows muscle from the Col13a1$^{LacZ/LacZ}$ mouse line stained for β-galactosidase to locate cells expressing type XIII collagen (A) and by α-bungarotoxin (α-BTX) to locate acetylcholine receptors (AChR) at the postsynaptic plasmamembrane (A') at the neuromuscular junction. Wild-type muscles were stained for type XIII collagen in immunoelectron microscopy (B-C).

Other Tissues with the Type XIII Collagen Expression in Adult and Fetal Mice

In addition to the non-sensitive method utilizing the β-galactosidase enzyme activity, location of lesser amounts of this reported can by identified by anti-β-galactosidase antibody stainings as done above for the NMJ. Staining was detected in many additional tissues. In the kidney (FIG. 4A) cells next to the glomerulus (FIG. 4A') are positive, and these cells could be juxtaglomerular cells participating in the renin-angiotensin system controlling blood pressure (data not confirmed). In the spleen staining localizes to the pericytes (cell type not confirmed) of the white pulp capillaries (FIG. 4B-B'). In the skin type XIII collagen is expressed by some rare cells of the hair follicles (FIG. 4C-D). In addition to the NMJ, the myotendinous junction (MTJ) of the muscle also contains type XIII collagen (FIG. 4E, published). In the eye the choroid layer (not confirmed) is locally positive for type XIII collagen expressing cells, and staining can be seen in the muscle behind the eye as well (FIG. 4F). The heart (FIG. 4G) shows some very local staining presumably locating at the left ventricle wall and the adjacent atrio-ventricular valve. In the intestine staining locates beyond the epithelial cell layer (FIG. 4H). In addition, at least brain (data not shown, but the staining pattern is similar to that in fetal tissues, in meninges, see FIG. 6) and lung tissues (figure not shown) are positive for anti-β-galactosidase staining in the Col13a1$^{LacZ/LacZ}$ mice.

FIG. 4A to H show anti-β-galactosidase antibody stainings of adult mouse tissues indicating the locations where type XIII collagen is expressed at low or moderate local concentrations. The tissues are as follows; kidney (A), spleen (B), skin (C-D), muscle (E), eye (F), heart (G) and intestine (H). In previous pictures, staining indicates type XIII collagen-expressing cells stained with the anti-β-galactosidase antibody, and the staining in pictures A' and B' indicates endothelial cells stained with the anti-PECAM antibody. The magnification in the picture varies a lot, but it is not indicated.

For some of the tissues there are no ready-made pictures of the anti-β-galactosidase antibody stainings, and for that reason some selected tissue are presented using anti-type XIII collagen antibodies on wild-type and knock-out tissues to show the specificity of the antibody staining. The tissue with the highest overall type XIII collagen expression by Western blotting, by measuring transcript levels (data not shown) and by immunostaining is the lung (FIG. 5A-B). The cell type expressing type XIII collagen is not identified. Also expression in the thyroid can be detected (FIG. 5C-D).

FIG. 5A to D show anti-type XIII collagen antibody stainings of selected additional adult mouse tissues from wild-type and knock-out mice. Wild-type lung (A) shows a strong expression lacking from the knock-out lung (B), and the same can be seen in wild-type (C) and knock-out (D) thyroid.

Additional adult mouse tissues found by Western blotting (data not shown) to express type XIII collagen are pancreas, liver, epididymis, salivary gland, adrenal gland, prostate and vas deference as presented in the Table I.

An overview of the type XIII collagen expression pattern in the mouse embryo was obtained by staining 16.5 dpc fetuses for type XIII collagen and β-galactosidase. Due to the low general expression levels of Col13a1-derived transcripts, the expression of β-galactosidase was best detected with an anti-β-galactosidase antibody, and this resulted in relatively specific staining patterns of heterozygous Col13a1$^{+LacZ}$ and homozygous Col13a1$^{LacZ/LacZ}$ fetuses (FIG. 6A). The anti-β-galactosidase staining showed the most prominent sites of Col13a1-driven expression to be all ossifying bone (arrowheads in FIG. 6A) and restricted areas of muscle representing developing myotendinous junctions (arrows in FIG. 6A). An anti-type XIII collagen antibody also stained strongly developing bone and myotendinous junctions in wild-type fetuses (FIG. 6B). Both antibodies further stained intensively pharynx, oesophagus, intestine and whisker follicles (FIGS. 6A and B). However, the β-galactosidase staining in intestine was more spot-like and restricted than the type XIII collagen staining, suggesting some unspecific staining with the anti-type XIII collagen antibody, while the β-galactosidase staining was more intense than the type XIII collagen staining in meninges and lung (FIGS. 6A and B) (Latvanlehto, 2004).

FIGS. 6 A and B describe anti-β-galactosidase antibody stainings of mouse fetal tissues. A Col13a1$^{LacZ}$ 16.5 dpc fetus from a heterozygous mating stained with an anti-β-galactosidase antibody (A), and a littermate wild-type control stained with the anti-type XIII collagen antibody. The panels are combinations of more than 100 individual pictures. Symbols; arrowheads indicate bone, arrows developing tendon, I, intestine, L, lungs, M, meninges, O, oesophagus, and P, pharynx. Bars, 1 mm.

EXAMPLE 2

Mice Deficient of Type XIII Collagen Exhibit Reduced Growth and Progressive Myopathy To study the biological function of the protein a mouse line lacking solely any type XIII collagen (Col13a1$^-$) was generated by removing the promoter, 5' UTR and first protein-coding exon of the type XIII collagen gene as presented in the example 1. Type XIII collagen knock-out mice were viable, fertile and had somewhat normal life-span. Homozygous mice were comparable to controls at birth but showed reduced growth at puberty (FIG. 7A). General condition of old knock-out mice regressed and mice developed progressive myopathy (arrows indicate central nuclei in FIG. 7C).

Altered Morphology Of The NMJ In Mice Deficient Of Intact Type Xiii Collagen Muscles from young (not shown) and old mice (FIGS. 8A and B) were stained for acetylcholine receptors and morphometric analysis was performed on NMJs. Junctions were small in size in young mice while they in elderly mice started to fragment earlier in knock-out than in control mice (FIGS. 8E and F). This phenomenon normally occurs in senescence and may associate with the progressive myopathy (FIG. 7C). Results indicated that type XIII collagen contributes to the stabilization of the NMJ structure.

Decreased Neuromuscular Response

Electromyography (EMG), an electrophysiological measurement to test the function of peripheral nerves and NMJ, showed an abnormal decrement in the NMJ response in type XIII collagen deficient mice (FIG. 8D) The symptom was not full-penetrance since only minority of the mice showed this defect. Nevertheless, we could show that the altered structure of the NMJ in the type XIII collagen deficient mice affects the function of the NMJ.

FIG. 7 A to C depicts the reduced growth of the type XIII collagen knock-out mice and a progressive myopathy in elderly mice. Female mice were weighted at ages indicated (A, week; wk, month; mth). Male mice showed similar growth rate. Histological stainings were performed on quadriceps muscles from 17-month-old mice (B-C). Progressive myopathy indicated by centrally located nuclei (arrows) was seen in old Col13a1$^{-/-}$ mice (C).

FIG. 8 A to F depicts morphometric analysis of the NMJ in the Col13a1$^{-/-}$ mice and the EMG. Quadriceps muscles from 17-month-old mice were stained with fluorescent α-bungarotoxin to locate acetylcholine receptors (A-B) and analyzed with a fluorescence microscope and the Analysis program. The acetylcholine receptor-positive junction area was measured from 3 and 17-month old knock-out mice and compared to controls (E). Number of the parts was also measured from the same samples (F). The response to repetitive stimulation in EMG at 30 Hertz was compromised in some of the mutant mice (D).

It was concluded that collagen XIII is a postsynaptic component of the neuromuscular junction. Lack of it leads to scattering of acetylcholine receptor clustering. Type XIII collagen thus seemed to function in maintenance of NMJ structure. Structural changes lead to electrophysically measurable decrement in nerve signal response of muscle. Similar changes in EMG were shown in human patient with myasthenia gravis.

EXAMPLE 3

Diagnosing MG by an In Vitro Method

Human sera: the patient sera were collected by Dr. Ritva Pirskanen at the Neurology Division, Department of Clinical Neuroscience, Karolinska Institutet, Karolinska University Hospital, Stockholm, Sweden. Patients are not treated with any immunosupressor and as a treatment about half of the patients were thymectomyced (32/62). According to "Myasthenia gravis Foundation of America Clinical Classification" (Jaretzki et al. 2000), 17 were classified in the class I, 38 in the class II, 4 in the class 3 and 2 in the class 4 (2 were nonclassified). The patient group consists of 40 females and 22 males. In the female group 2 were under 20, 16 were 20-40, 9 were 41-60, 12 were 61-85, and 1 was over 85 years of age. In the male group 3 were 20-40, 6 were 41-60, and 13 were 61-85 years of age. The control sera with the age and gender collated were collected by Dr. Ritva Pirskanen-Matell and Dr. Juha Risteli at the Department of Clinical Chemistry, University of Oulu, Finland. Other serum samples were collected randomly from several volunteers in the Department of Medical Biochemistry and Molecular Biology, University of Oulu ELISA test of human sera: Human recombinant type XIII collagen protein was produced by a published protocol (Tu et al., 2002) with the following modification. High Five insect cells (Invitrogen) were co-infected with a virus encoding human type XIII collagen and another one encoding the human prolyl 4-hydroxylase. The type XIII collagen protein was purified from 48-72 hour infected culture media sequentially using a HiTrap Q 5 ml column (Amersham Bioscience), a Hitrap SP 5 ml column (Amersham Bioscience) and a Superdex 200 column (Amersham Bioscience). The protein purity was verified by SDS-PAGE, N-terminal protein sequencing, and amino acid composition analysis. For ELISA testing 5 μg/ml of type XIII collagen was coated onto a 96-well microplate over night at 4° C. BSA 10 μg/ml and type I collagen 10 μg/ml were also coated for negative controls. The uncoated space was then blocked with 8% no-fat milk in PBS for 1 hour at room temperature. Human sera were diluted 1:50, 1:100 and 1:500 in the blocking reagent, and incubated with the immobilized type XIII collagen for 2 hours at room temperature. After a thorough wash step, a horseradish peroxidase (HRP) conjugated anti-human IgG antibody was added to the plate and incubated for 1 hour at room temperature. The excess antibody was washed away, and an HRP substrate TMB was added for detection at 450 nm.

Western blotting analysis: Recombinant type XIII collagen 0.3 μg was loaded onto a 7.5% SDS-PAGE gel under a reducing condition. After electrophoresis, the protein bands were electroblotted onto a nitrocellulose membrane. The membrane was then blocked with 8% no-fat milk in PBS for 1 h at room temperature and incubated with human sera 1:100 diluted in the blocking solution or with a type XIII collagen monoclonal antibody (VTT, Finland) 1:1000 diluted in the same solution for 1 h at room temperature. After a thorough wash step, the membrane was incubated with a HRP-conjugated anti-human (for human sera) or anti-mouse (for monoclonal antibody) IgG (Jackson ImmunoResearch, PA., USA) diluted 1:10000 in the blocking solution for 1 h at room temperature, and then the detection was performed using an ECL kit (GE Healthcare).

FIG. 9 shows the result of ELISA screening, where the antibody titer against type XIII collagen versus the age of onset of MG in patients is indicated. 27 control samples ±2×standard deviation is shown as a grey area. For patients' sera seronegativity against acetyl choline receptors (AChRs) is indicated as circle or triangular and gender as filled or open symbols. The normal control sera were from the Neurology Division, Department of Clinical Neuroscience, Karolinska Institutet, Karolinska University Hospital, Stockholm, Sweden and from the Department of Clinical Chemistry, University of Oulu with collated gender and age. 10 samples showed positive serum autoimmune-antibodies for type XIII collagen. Out of those 10, 6 were negative for anti-AChR autoimmune-antibodies and all 5 tested negative for anti-muscle specific kinase (MuSK) autoimmune-antibodies (1/9 seronegative MG patients and 0/4 controls was positive for anti-MuSK autoimmune-antibodies, analyzed by Professor Angela Vincent, Weatherall Institute of Molecular Medicine, John Radcliffe Hospital, UK). Out of the patients positive for anti-collagen XIII autoimmune-antibodies one was classified in the disease class I and the other 9 in the class II. Statistically significant correlation between anti-type XIII collagen XIII autoimmune-antibody positivity and seronegativity against anti-AChR autoimmune-antibodies was found (p=0.03), but not when correlating anti-type XIII collagen antibody-positivity with AChR-antibody titer, age of thymectomy, classification of the disease, disease time, age of onset and gender.

Figure 10:
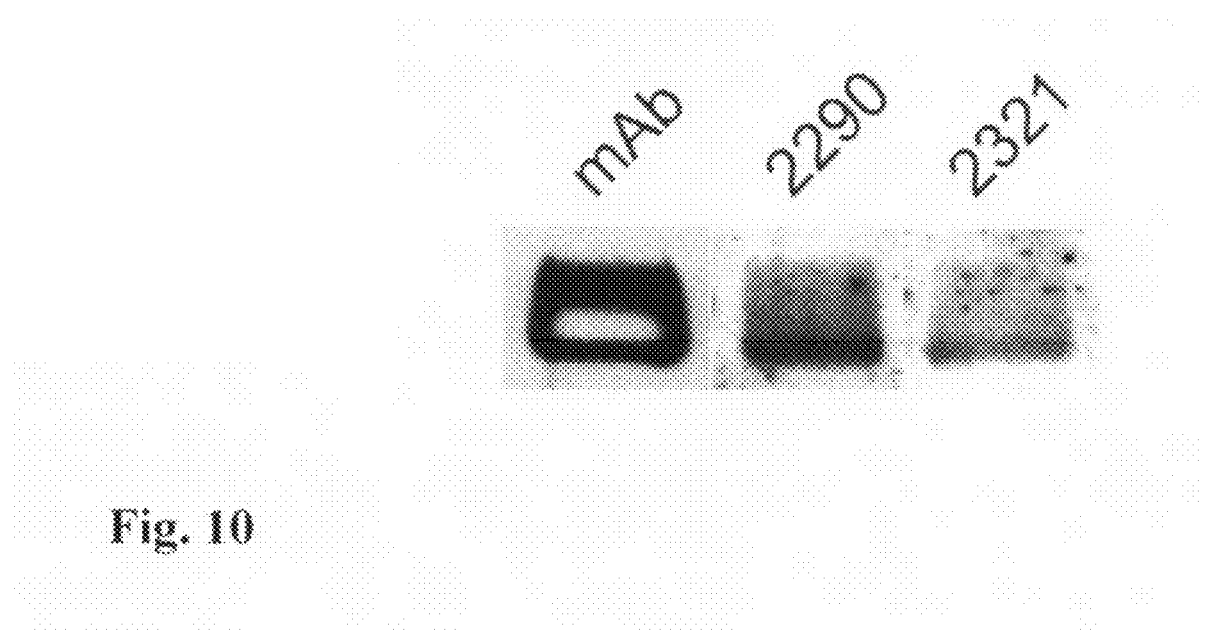
FIG. 10 Western blotting confirms that the autoimmune antibodies in patient sera specifically recognized type XIII collagen.

Western blotting in FIG. 10 confirmed that the autoimmune antibodies in patient sera specifically recognized type XIII collagen. Unpurified sera from the patients #2290 and #2321 recognize recombinant type XIII collagen protein in a similar manner when compared with a monoclonal type XIII collagen antibody (mAb, Tu et al., 2002).

Figure 11:
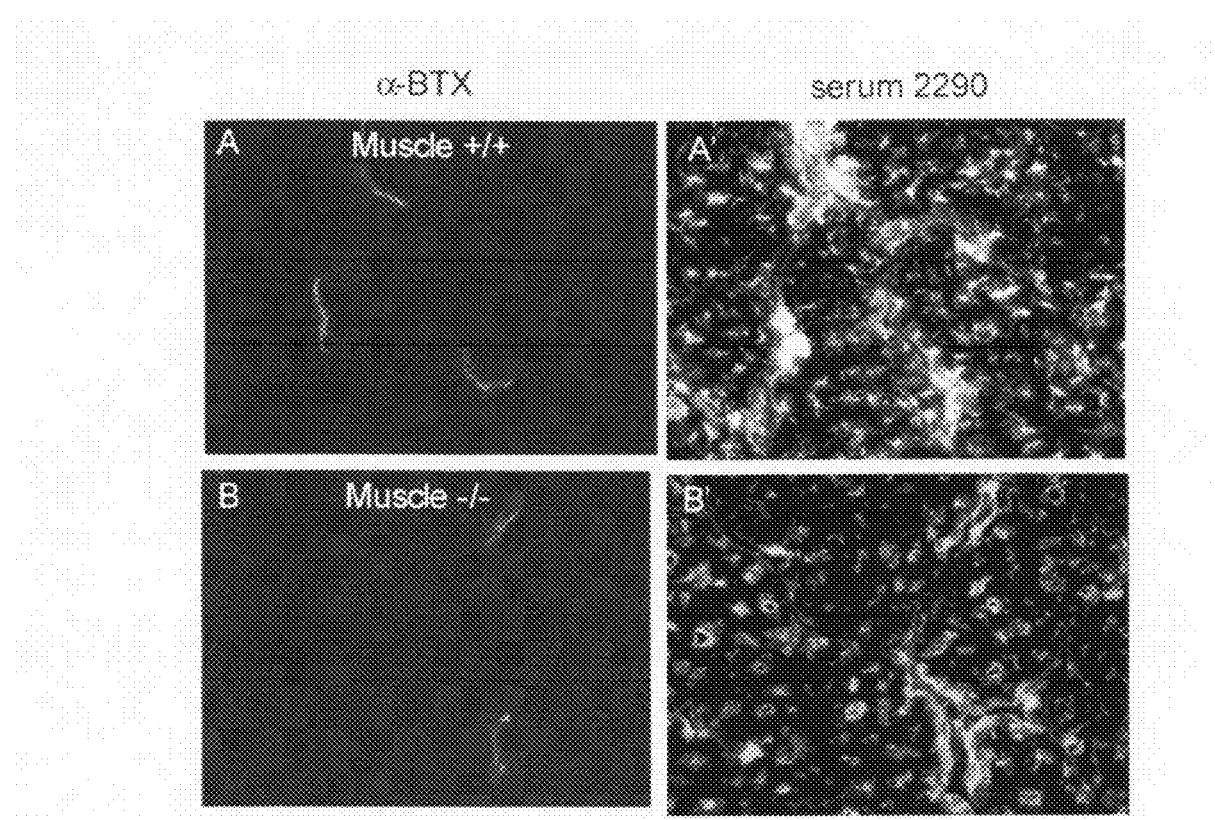
FIG. 11 Immunostaining of mouse muscle tissue confirms that the autoimmune antibodies in patient sera specifically recognized type XIII collagen.

To prove the pathogenic autoimmune-antibodies in patient's sera specific for type XIII collagen, an unpurified serum from the patient #2290 (antibody titer 0,982, see FIG. 9) was used to stain mouse muscle. The patient serum recognizes NMJs in a muscle from wild-type mouse (FIG. 11A') but not in a muscle from type XIII collagen deficient mouse (11B') thus showing that autoimmune-antibodies are against type XIII collagen at the NMJ. Muscles were double-stained with α-BTX (11A and B) to locate NMJs.

Human sera showed high background (non-specific binding) in both ELISA and Western blotting analyses with conventional protocols. Here we increased the milk concentration to 8% for blocking, which reduced the background significantly. However, other blocking reagents can also be used.

We used TMB as the substrate for HRP in ELISA detection. Another more sensitive method, which could be used here, is for example chemiluminescence detection.

REFERENCES

De Bellis, A, D Sansone, C Coronella, M Conte, S Iorio, S Perrino, M Battaglia, G Bellastella, J R Wall, A Bellastella, A Bizzarro, 2005, Serum antibodies to collagen XIII: a further good marker of active Graves' ophthalmopathy: Clin. Endocrinol. (Oxf), v. 62, p. 24-29.

Gossler, A, J Zachgo, 1993, Gene and enhancer trap screens in ES cell chimeras, in A L Joyner (ed), Gene Targeting-A practical Approach: New York, Oxford University Press, p. 181-234.

Hägg, P, M Rehn, P Huhtala, T Väisänen, M Tammisto, T Pihlajaniemi, 1998, J Biol Chem. 273:15590-7.

Hägg, P, T Väisänen, A Tuomisto, M Rehn, H Tu, P Huhtala, S Eskelinen, T Pihlajaniemi, 2001, Type XIII collagen: a novel cell adhesion component present in a range of cell-matrix adhesions and in the intercalated discs between cardiac muscle cells: Matrix Biology, v. 19, p. 727-742.

Jaretzki A, Barohn R J, Emstoff R M, et al. (2000). "Myasthenia gravis: recommendations for clinical research standards. Task Force of the Medical Scientific Advisory Board of the Myasthenia Gravis Foundation of America". Neurology 55(1): 16-23.

Juvonen, M, T Pihlajaniemi, H Autio-Harmainen, 1993, Location and alternative splicing of type XIII collagen RNA in the early human placenta: Laboratory Investigation, v. 69, p. 541-551.

Kvist, A P, A Latvanlehto, M Sund, L Eklund, T Väisänen, P Hägg, R Sormunen, J Komulainen, R Fässler, T Pihlajaniemi, 2001, Lack of cytosolic and transmembrane domains of type XIII collagen results in progressive myopathy: Am J Pathol, v. 159, p. 1581-1592.

Kvist, A P, A Latvanlehto, M Sund, N Horelli-Kuitunen, M Rehn, A Palotie, D Beier, T Pihlajaniemi, 1999, Complete exon-intron organization and chromosomal location of the gene for mouse type XIII collagen (col13a1) and comparison with its human homologue: Matrix Biology, v. 18, p. 261-274.

Latvanlehto, A. Type XIII collagen; Organization of the mouse gene, generation of three genetically engineered mouse lines by homologous recombination, and biochemical studies on the molecular properties of the type XIII collagen protein. 2004. Oulu, Oulu University Press. Acta Univ. Oul. D811.

Nagy, A, J Rossant, R Nagy, W Abramow-Newerly, J C Roder, 1993, Derivation of completely cell culture-derived mice from early-passage embryonic stem cells: Proceedings of the National Academy of Sciences of the United States of America, v. 90, p. 8424-8428.

Peltonen, S, M Hentula, P Hägg, H Ylä-Outinen, J Tuukkanen, J Lakkakorpi, M Rehn, T Pihlajaniemi, J Peltonen, 1999, A novel component of epidermal cell-matrix and cell-cell contacts: transmembrane protein type XIII collagen: J Invest Dermatol., v. 113, p. 635-642.

Potocnik, A J, C Brackebusch, R Fässler, 2000, Fetal and adult hematopoietic stem cells require β1 integrin function for colonizing fetal liver, spleen, and bone marrow: Immunity, v. 12, p. 653-663.

Sakai, K, J Miyazaki, 1997, A transgenic mouse line that retains Cre recombinase activity in mature oocytes irrespective of the cre transgene transmission: Biochem Biophys Res. Commun., v. 237, p. 318-324.

Sandberg-Lall, M, P O Hägg, I Wahlström, T Pihlajaniemi, 2000, Type XIII collagen is widely expressed in the adult and developing human eye and accentuated in the ciliary muscle, the optic nerve and the neural retina: Experimental Eye Research, v. 70, p. 401-410.

Sandberg, M, M Tamminen, H Hirvonen, E Vuorio, T Pihlajaniemi, 1989, Expression of mRNAs coding for the α1 chain of type XIII collagen in human fetal tissues: comparison with expression of mRNAs for collagen types I, II, and III: Journal of Cell Biology, v. 109, p. 1371-1379.

Sund, M, T Väisänen, S Kaukinen, M Ilves, H Tu, H Autio-Harmainen, H Rauvala, T Pihlajaniemi, 2001, Distinct expression of type XIII collagen in neuronal structures and other tissues during mouse development: Matrix Biol, v. 20, p. 215-231.

Tu, H, S Sasaki, A Snellman, W Göhring, P Pirilä, R Timpl, T Pihlajaniemi, 2002, The type XIII collagen ectodomain is a 150-nm rod and capable of binding to fibronectin, nidogen-2, perlecan, and heparin: J Biol Chem, v. 277, p. 23092-23099.

Ylönen, R. Characterization of the function of type XIII collagen in mice; specific roles during cardiovascular development and posnatally in bone modelling. 2005. Oulu, Oulu University Press. Acta Univ. Oul. D862.

Ylönen, R, T Kyrönlahti, M Sund, M Ilves, P Lehenkari, J Tuukkanen, T Pihlajaniemi, 2005, Type XIII collagen strongly affects bone formation in transgenic mice: Journal of Bone & Mineral Research, v. 20, p. 1381-1393.

What is claimed is:

1. A method for diagnosing human diseases myasthenia gravis, said method comprising the steps of:
providing a biological sample from a patient having symptoms of or suspected to have a disease affecting the tissues of organs selected from the group consisting of spleen, brain, heart, kidney, thyroid, eye, skin, intestine, liver, pancreas, adrenal gland, prostate and lungs or tissues of bones, muscle or other tissues;
determining the amount of autoimmune-antibodies against type XIII collagen in the biological sample, and
comparing the amount of autoimmune-antibodies in the sample to the amount of autoimmune-antibodies in a biological sample of a group of control people not having symptoms of the disease to be diagnosed;
wherein an increase of the amount of autoimmune-antibodies in the sample compared to the amount of autoimmune-antibodies in the sample of a group of control people is indicative of myasthenia gravis.

2. The method of claim 1, wherein the disease affects the neuromuscular junctions.

3. The method according to claim 1, wherein the biological sample is a serum and/or plasma sample.

4. The method according to claim 1, wherein the determination of the amount of autoimmune-antibodies is carried out by immunoassay, such as an ELISA method.

5. The method of claim 1 for diagnosing human diseases, wherein type XIII collagen protein or parts thereof, and optionally a positive and/or a negative control are provided on a kit.

6. The method of claim 5, wherein said positive control is an antibody of type XIII collagen and said negative control is healthy serum and/or plasma pool.

* * * * *